(12) United States Patent
Patitucci et al.

(10) Patent No.: US 10,636,400 B2
(45) Date of Patent: Apr. 28, 2020

(54) METHOD FOR PRODUCING AND STREAMING MUSIC GENERATED FROM BIOFEEDBACK

(71) Applicants: Joseph William Patitucci, Marina Del Rey, CA (US); Jonathan Shapiro, Marina Del Rey, CA (US)

(72) Inventors: Joseph William Patitucci, Marina Del Rey, CA (US); Jonathan Shapiro, Marina Del Rey, CA (US)

(*) Notice: Subject to any disclaimer, the term of this patent is extended or adjusted under 35 U.S.C. 154(b) by 0 days.

(21) Appl. No.: 16/424,419

(22) Filed: May 28, 2019

(65) Prior Publication Data

US 2019/0333487 A1 Oct. 31, 2019

Related U.S. Application Data

(60) Provisional application No. 62/662,730, filed on Apr. 25, 2018.

(51) Int. Cl.
*G10H 1/00* (2006.01)
*G10H 1/14* (2006.01)
*A61B 5/024* (2006.01)
*A61B 5/00* (2006.01)

(52) U.S. Cl.
CPC ....... *G10H 1/0025* (2013.01); *A61B 5/02438* (2013.01); *A61B 5/6801* (2013.01); *A61B 5/7264* (2013.01); *G10H 1/0066* (2013.01); *G10H 1/14* (2013.01); *G10H 2210/325* (2013.01); *G10H 2210/391* (2013.01); *G10H 2220/101* (2013.01); *G10H 2220/371* (2013.01)

(58) Field of Classification Search
CPC ...... G10H 1/0025; G10H 1/0066; G10H 1/14; G10H 2220/101; G10H 2210/325; G10H 2220/371; G10H 2210/391; A61B 5/7264; A61B 5/6801; A61B 5/02438; A61B 5/486
USPC .......................................................... 84/609
See application file for complete search history.

(56) References Cited

U.S. PATENT DOCUMENTS

| | | | | |
|---|---|---|---|---|
| 5,253,168 A * | 10/1993 | Berg | .................... | A61B 5/4857 128/905 |
| 5,267,942 A * | 12/1993 | Saperston | ............. | A61M 21/02 128/905 |
| 5,321,350 A * | 6/1994 | Haas | ...................... | G01R 23/02 324/76.11 |
| 5,692,517 A * | 12/1997 | Junker | .................. | A61B 5/0482 600/545 |
| 6,487,817 B2 | 12/2002 | Airaudi | | |
| 6,893,407 B1 * | 5/2005 | Brooks | .................. | G06F 3/016 600/300 |
| 7,207,935 B1 * | 4/2007 | Lipo | ........................ | A61B 5/16 600/28 |
| 2006/0084551 A1* | 4/2006 | Volpe, Jr. | ........... | A63B 71/0686 482/8 |

(Continued)

*Primary Examiner* — Jeffrey Donels
(74) *Attorney, Agent, or Firm* — Keeley DeAngelo LLP; W Scott Keeley

(57) ABSTRACT

A method for producing and streaming music generated from biofeedback. The method employs machine-readable language instructions that alter received signals from a wearable biofeedback device, generating musical tones to be played on a portable electronic device and/or shared with others. The varying musical tones that are produced by the method can be modulated by the user to reach a targeted state of emotion.

8 Claims, 5 Drawing Sheets

(56) References Cited

U.S. PATENT DOCUMENTS

| | | | |
|---|---|---|---|
| 2006/0102171 A1* | 5/2006 | Gavish | A61B 5/0816 128/95.1 |
| 2006/0111621 A1* | 5/2006 | Coppi | A61B 5/222 600/300 |
| 2011/0021318 A1* | 1/2011 | Lumsden | A63B 69/00 482/8 |
| 2012/0316453 A1* | 12/2012 | Marcarian | A61B 5/0488 600/546 |
| 2014/0302471 A1* | 10/2014 | Hanners | G09B 19/003 434/247 |

* cited by examiner

METHOD FOR PRODUCING AND STREAMING MUSIC GENERATED FROM BIOFEEDBACK

TECHNICAL FIELD

The present disclosure relates to a method of producing and streaming music generated from biofeedback.

BACKGROUND

Methods and devices that detect biological variations in humans have been in use since the late 1800s. "Biofeedback" systems were developed to detect human physiological functions such as heart rate and translate them into an output that allowed people to observe and manipulate them. Devices used in these systems include electroencephalographs (EEGs), which measure the electrical activation of the brain from scalp sites across the human cortex; and electrocardiograms (ECGs), which use electrodes attached to the human body to measure the electrical activity of the heart. Two types of heart-activity measurements are heart rate (or interbeat intervals) and heart-rate variability (or statistical variability of interbeat intervals).

Over the last 40 years, methods and devices that detect human heart beat and heart-rate variability have been employed in the study of nervous-system function and cognitive and emotional changes in people. This research is used to study human ability to adapt effectively to environmental stress.

From the discovery of biofeedback grew the invention of musical generation from biofeedback. With the availability of a Musical Instrument Digital Interface (MIDI) platform in the 1980s, methods and computer devices have been developed to generate musical tones from human biorhythms by use of these MIDI sound generators and synthesizers.

MIDI information includes MIDI note and continuous-controller (MIDI CC) messages. A MIDI Processor processes MIDI through a master clock, MIDI bus and MIDI effects.

MIDI effects include MIDI signal processors, which include MIDI scalers, MIDI pitch effects, MIDI delays and note echoes, MIDI chord processors, arpeggiators, note-length effects and other effects.

MIDI scalers limit MIDI note data streams to a specific scale or key.

MIDI pitch effects determine the base pitch of a note and can be used to change the octave of a specific instrument or to change the interval relationship between one MIDI note stream and another.

Arpeggiators define the number of MIDI notes that can be expressed per measure.

An audio master mixes the output of various MIDI instruments.

MIDI Instruments are sample-based instruments, oscillators or tone generators.

Audio effects include audio signal processors such as delay, reverb, distortion, overdrive, bit crushers, filters, resonators, panning vibrato, tremolo, compressor, and other effects.

Presets are specific configurations of MIDI Instruments, MIDI effects and audio effects.

Biofeedback is the process of gaining awareness of physiological functions using instruments that provide information on the activity of those systems, with a goal of being able to manipulate them at will.

The term "biodata" is used here to describe data that depicts human states of consciousness as output by wearable biofeedback devices.

Portable electronic devices include smartphones, tablet devices and the like.

Algorithms are processes or sets of rules to be followed in calculations or other problem-solving operations, especially by a computer.

A logarithm is a quantity representing the power to which a fixed number must be raised to a given number. In this embodiment, logarithmic functions are applied to values generated from a biofeedback device, resulting in specific ranges of control messages which, together with MIDI note messages, are translated into musical tones by a MIDI server.

Signal-chain processing refers to a flow of control from one input to another. Output from one portion of the chain supplies input to the next. In this context signal-chain processing refers to the intentional alteration of audio signals.

Sonification refers to the generating of musical tones from data.

Note-shifting is the use of MIDI software to shift musical notes.

Artificial intelligence (AI) is intelligence demonstrated by machines.

A "computer readable-medium" is also known as software.

SUMMARY

A method for producing and streaming music generated from biofeedback.

The platform employs a set of machine-readable language instructions (hereafter referred to as software) that receives physiological signals from a wearable biofeedback device worn by a person. The method's software analyzes this feedback and translates the biofeedback data or "biodata" to MIDI information. The method then generates musical sequences which are output through the speakers of the apparatus, or through a linked portable electronic device.

Biodata produced from a wearable biofeedback device is sent to a portable electronic device. The software analyzes output from the wearable device, applying specific algorithms, a MIDI processor, MIDI instruments and audio effects to produce varying musical tones, which are amplified through the device or through speakers paired with the device.

A biofeedback device delivers biometrics that can be measured against a biometric target. This relationship controls the method's audio effects. The method maps controls from a biofeedback device by creating an obvious shift in tone for the relationship between the generated biometric and a target biometric. An example of shifts between the relationships are note octaves, MIDI effects and audio effects. The octave shift is carried out by, for example, a note-shift function in the method's software.

Biometric output from a wearable biofeedback device determines specific ranges of control messages (CCs) and octave controls. CCs are generated by performing a logarithmic function on biometric output from the wearable biofeedback device. The CCs are then mapped to various parameters. This is explained in detail below.

During software analysis a master clock determines tempo in beats per minute or in samples per second. A MIDI bus takes the MIDI note and continuous-controller (CC) messages from the algorithm and busses them to multiple MIDI channels.

Within each MIDI channel, MIDI notes are run through a series of MIDI effects. The MIDI notes are then sent to MIDI instruments. The resulting audio data is sent to an audio master.

An audio master uses an audio mixer to mix the output of the various MIDI instruments and includes volume and panning controls. Master audio effects are applied to the mix of MIDI instruments, producing a master output, which is sent to the portable electronic device as musical tones.

The above steps are described in more detail in an example embodiment. In such an embodiment the system and apparatus converts data from a wearable biofeedback device into music. An example biofeedback device might be a heart-rate and heart-rate-variability detector. To create musical tones from the biofeedback device's output, the system and apparatus performs the following steps:

1. Applies an algorithm to translate biodata to MIDI note and MIDI CC values
2. Runs the MIDI note and MIDI CC values through a MIDI processor
3. Resulting MIDI notes and MIDI CC values control MIDI instruments
4. MIDI instruments are run through audio effects
5. MIDI instruments and audio effects are sent through a virtual mixer, resulting in an audio output
6. Audio is output via a graphical user interface to a speaker or a speaker of a portable electronic device.

To generate MIDI notes (Step 1, above), the method reads biodata from a wearable device as numbers. The numbers represent interbeat intervals (Mb) of a heartbeat. These numbers are used to create MIDI note values to control pitch. The system's algorithm analyzes relationships between numbers and assigns those relationships a numerical value. For example if the numerical value between incoming heartbeats (IBIs) is increasing, it indicates a slowing heart rate. The value of this IBI is then used as the input in the next step.

In this step, that numerical value is compressed to fall within a specific note range using a mod function. A mod function is used to determine a range of notes. If the desired range were an octave, a mod-12 function would be applied, and any notes would fall within a single octave. When the desired effect is to have all notes fall within a three-octave range (1-36), a mod-36 function would be applied.

A IBI of 300 ms arriving after one of 450 ms results in an IBI variation (IBIV) of 150 ms. A mod 12 function (dividing the IBIV by 12 and using the remainder to multiply by 12), is applied to the IBIV. The result is a number that is always between 0 and 11, thus creating an octave. For example: 150 mod 12 is 6; 100 mod 12 is 4; 2 mod 12 is 2; 12 mod 12 is 0; 13 mod 12 is 1; and 14 mod 12 is 2.

The compressed numbers are then sent into a MIDI processor to be played by virtual instruments with timbre and rhythmic components controlled by MIDI CC values.

In Step 2 (above), MIDI CC values are determined in one of two ways:

1. From raw numbers: the method's algorithm analyzes relationships between raw numbers and assigns those relationships a numerical value between 0-127.
2. From a scoring algorithm: the method's algorithm is tuned to a scoring algorithm coming from the wearable, or from a third-party app controlled by the wearable. The method's algorithm extrapolates scoring ranges into numerical ranges between 0-127. It does this by dividing 128 by a target number. A target number might be a target biometric, such as a heart rate (e.g., 190 beats per minute) or the potential high score of a fitness-related game. In the example of target heart rate, then, 128 divided by 190=0.673468. That number is called a point value. A point value is the value of a single point in a fitness game or the number 1 related to a target biometric.

A current number is defined as the current biometric measurement from a wearable device (e.g., a current heart rate of 50 bpm as measured by the device) or a person's current score in a fitness-related game. To determine a CC number, the method multiplies the point value by the current number (e.g., 50 bpm). Thus a point value of 0.673468 times a current number of 50 equals a CC number of 33.68, which would be rounded to CC34. A heart rate of 180 bpm would have a value of 121.26, which would be rounded to CC121.

In a fitness-game scenario, a highest score (or target number) is 100. The point value would then be 1.28 (128/100). A score of 1 would produce a value of 1.28, which would be rounded to CC1. A score of 10 would produce a value of 12.8, which would be rounded to CC13. And a score of 90 would produce a value of 115.2, which would be rounded to CC115.

The above algorithm is depicted thus:

$$CC = PV \times CN - R \text{ where}$$
$$R = \begin{cases} 0, & \text{if } PV * CN \leq 1.28, \\ (PV * CN - 128), & \text{if } PV * CN > 128. \end{cases}$$

In Step 3, MIDI note and MIDI CC values are sent from this algorithm to the MIDI processor to control pitch, timing and timbre qualities of digital instruments. In the MIDI processor, MIDI notes are run through an array of MIDI effects, some of which are modulated by the MIDI CC data. The output of the MIDI Processor is MIDI note and MIDI CC data.

The MIDI processor consists of:

A clock, which determines the tempo of all time-based MIDI effects;

MIDI scalers, which scale all MIDI notes to a specific key (e.g., A-pentatonic).

Arpeggiators, which control the timing at which note messages are sent from the MIDI processor to digital instruments;

Note wrapping, which defines the lowest note and octave range of MIDI notes;

MIDI transposition effects, which shift a MIDI note from its input value to a new output value. For instance, a MIDI note message can come in at a value of 60, which is C4 or middle C, and be pitched +12 to a value of 72, or C5 (one octave above middle C).

MIDI CC data can control parameters of components of the MIDI processor and can control whether those components are active. For instance, MIDI CC data can be mapped to control the clock/tempo within a certain range, or it can be used to control arpeggiators within a certain range; and it could be used to turn on and off components of the MIDI processor.

MIDI note and MIDI CC messages output from the MIDI processor are sent to control MIDI Instruments.

In Step 4, MIDI instruments are controlled by MIDI note and MIDI CC messages.

The output of MIDI instruments is audio.

MIDI Instruments can be built in three ways:

Through sound synthesis;

As sample-based instruments where a sample of a single root note is pitched/shifted to create other notes;

A combination of sample-based instrumentation and synthesis.

MIDI CC values are used to modify the sounds of the MIDI instruments by using ranges of CC data to:

Change parameters on a synthesizer (for instance, attack, decay, sustain and release);

Turn on/off MIDI instruments;

To toggle between instruments.

In Step 5, audio from the output of MIDI instruments is sent to the method's audio effects. There, audio from the MIDI instruments is processed into audio that is output to a user. Examples of audio effects include gain, reverb, delay, distortion, bit-crushing, filtering, equalizing and resonating.

MIDI CC data is used to change parameters and/or activation of audio effects. For instance, thresholds of MIDI CC data can be used to:

Change the depth or wetness of a reverb, or change the rate, feedback or depth of a delay;

Turn on and off effects modules;

Toggle between effects modules.

In an example embodiment, biodata sonification software is hosted on the method's server. This software employs a biodata-to-MIDI converter and a sound engine comprised of MIDI instruments.

A user accesses that biodata sonification software through a web page or a smartphone app. The biodata sonification software recognizes the user's wearable biofeedback device and pairs (connects) with it, allowing biodata to stream from the wearable device to the user's portable electronic device.

The method's software converts received biodata into MIDI information through an algorithm in the biodata sonification software. This MIDI information controls MIDI instruments in the biodata sonification software. A user can listen to the sounds generated through the MIDI instruments through their portable electronic device or through any paired audio device.

The user may then choose to stream MIDI information to the method's server for other users to stream. Other users can access the biodata sonification software on the method's server through the method's web page or smartphone app. They can stream the MIDI information from the server to their portable electronic devices so that it can control the MIDI instruments on the biodata sonification software that they have installed on their portable electronic device.

In another example embodiment, a user downloads the method's biodata sonification app to their portable electronic device. The biodata signification app includes a biodata-to-MIDI converter and a sound engine made up of MIDI instruments.

The user pairs their wearable device with the biodata sonification app on their portable electronic device, and biodata is streamed from an attached wearable device to the user's portable electronic device, which runs the biodata sonification app. Biodata is converted into MIDI information through an algorithm in the biodata sonification app, and this MIDI information controls MIDI instruments that produce musical tones. Listening through their portable electronic device/phone or paired audio device, the hears musical tones generated through the MIDI instruments.

The user may then choose to stream MIDI information to the method's server for other app users to stream.

Other app users may stream the MIDI information from the server to their portable electronic devices so that it can control the MIDI instruments on the biodata sonification app on their portable electronic device/phone.

A software-based sound engine employs machine learning to calibrate and develop a custom set of biometric data—a profile—that is unique to each user. The sound engine contains an artificial intelligence (AI) component that measures how a user is responding to produced sounds. The AI chooses among musical presets and measures the user's response to them. In this way the AI learns which sounds to play to achieve the effect defined by the user.

Learned data is saved and shared across the platform to allow the AI to draw from a large sample set when selecting sounds for each new user.

The software further allows users to upload their MIDI to an Internet cloud server, where it may be streamed by others.

The varying musical tones that are produced by the method make a continuous stream of tones that can be modulated by the user's biometrics. Directed modulations in texture or patterns of sound serve to induce desired states of emotion. For example, a user might choose from a set of sounds offered by the software interface to induce a state of alertness. Using a chosen set of sounds as a musical construct, the user listens to the musical tones and modulates his or her biofeedback to influence the musical tones. As a user's biofeedback enters biometric states associated with alertness, he or she is "rewarded" with pleasing sounds to their user-defined musical preference.

BRIEF DESCRIPTION OF THE DRAWINGS

The references below are made to assist those of skill in the art in making and using the disclosed method.

Any of these embodiments are understood to be non-exclusive and interchangeable.

DESCRIPTION

Figure 1:
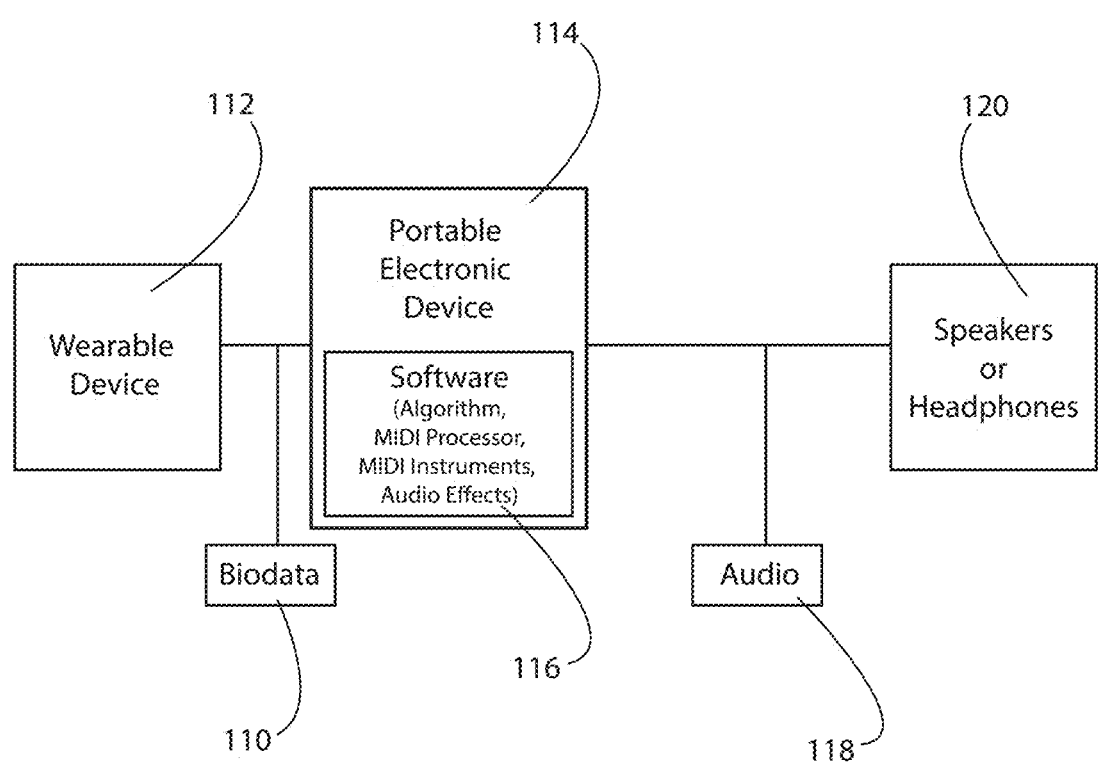
FIG. 1 is an illustration of an example embodiment.

Referring to FIG. 1, in example embodiment 100: Biodata 110 produced from a wearable biofeedback device 112 is sent to a portable electronic device 114. On the device, software 116 recognizes the connection and loads. The software analyzes output from the wearable device 112, employing specific algorithms, a MIDI processor, MIDI instruments and audio effects to produce audio 118 in the form of varying musical tones which are amplified through the device 114 or through speakers 120 paired with the device.

Figure 2:
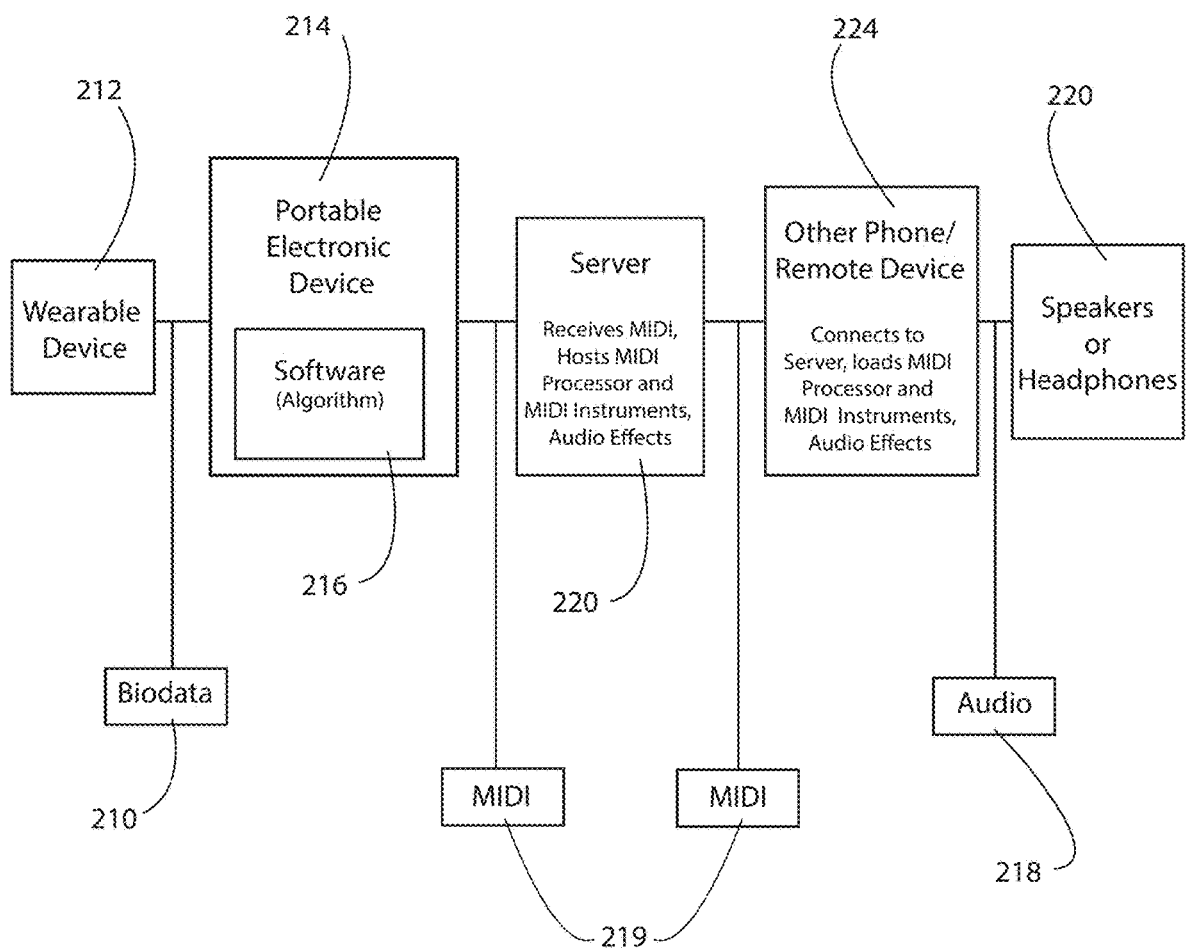
FIG. 2 illustrates a second embodiment.

Referring to FIG. 2, in example embodiment 200: Biodata 210 produced from a wearable biofeedback device 212 is sent to a portable electronic device 214. On the portable electronic device, software 216 recognizes the connection and loads. The software analyzes output from the wearable device 212 and applies specific algorithms, producing MIDI information. The embodiment's software uploads MIDI information to a central server 220 which also hosts MIDI processors, MIDI instruments and audio effects.

The MIDI information, along with MIDI processors, MIDI instruments and audio effects are then loaded to any number of other users' devices 224. The embodiment's software, which any number of users has loaded onto their devices, connects to the server 220, streams the MIDI information 219 and processes the MIDI information through the MIDI processor. The resulting MIDI is used to control the MIDI instruments. Resulting audio in the form of musical tones 218 is then amplified through these devices or through speakers 220 paired with the devices.

Figure 3:
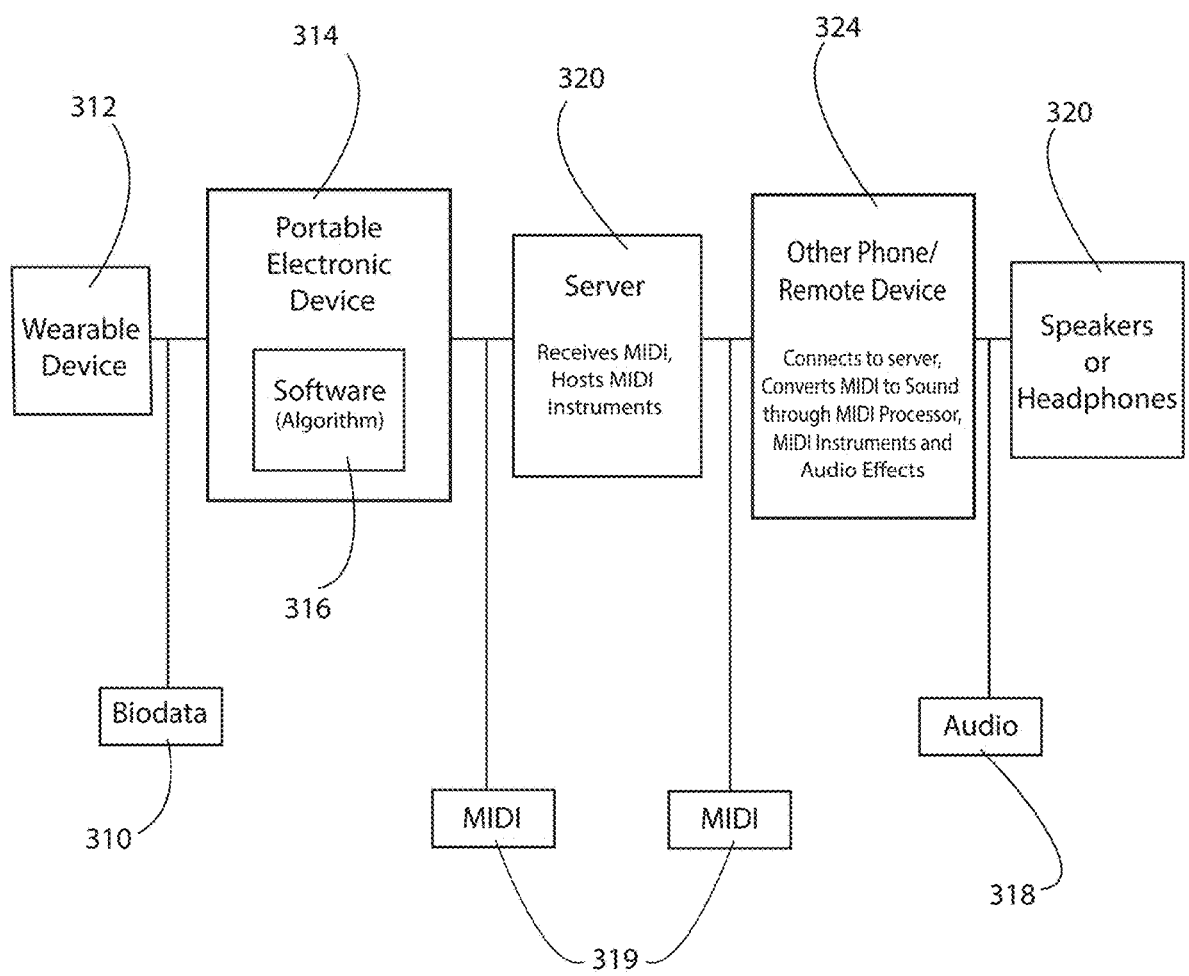
FIG. 3 represents a third embodiment.

In FIG. 3, example embodiment 300: Biofeedback data 310 produced from a wearable biofeedback device 312 is sent to a portable electronic device 314. Software 316 on the device recognizes the connection and loads. The software analyzes output from the wearable device 312 and applies specific algorithms to produce MIDI information 319. The embodiment's software uploads MIDI information to a central server 320. The MIDI information is then streamed to any number of other users' devices 324 that have the embodiment's software loaded. These devices connect to the server 320 and stream MIDI information. On each device, the MIDI stream 319 is sent to the MIDI processor 324 and the resulting MIDI controls MIDI instruments which produce sound. Resulting audio 318 in the form of musical tones are amplified through the devices or through speakers 320 paired with the devices.

Figure 4:
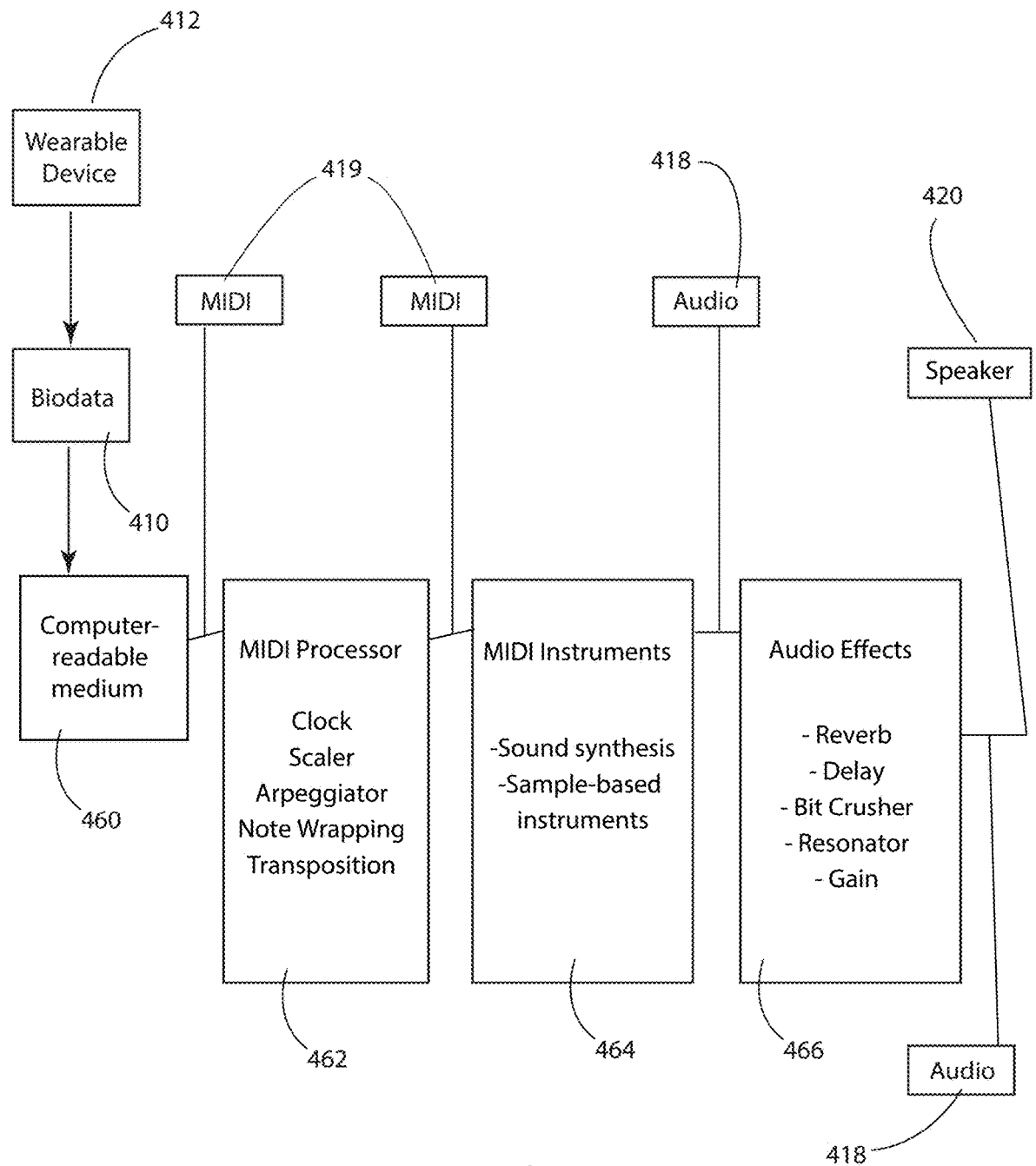
FIG. 4 represents a fourth embodiment.

Referring to FIG. 4, in example embodiment 400: Biodata 410 produced from a wearable biofeedback device 412 is received by a computer readable-medium (aka software) 460. The software analyzes biodata 410 and applies specific algorithms to produce MIDI information 419. A MIDI processor 462 applies the functions of clock, scaler, arpeggiator, note-wrapping and transposition. MIDI instruments 464 add sound synthesis and sample-based instruments to the data. Audio 418 is generated and audio effects 466 are added. Audio effects 466 include reverb, delay, bit-crusher, resonator, gain and the like. The resultant data is output to audio 418 and sent to a speaker 420.

Figure 5:
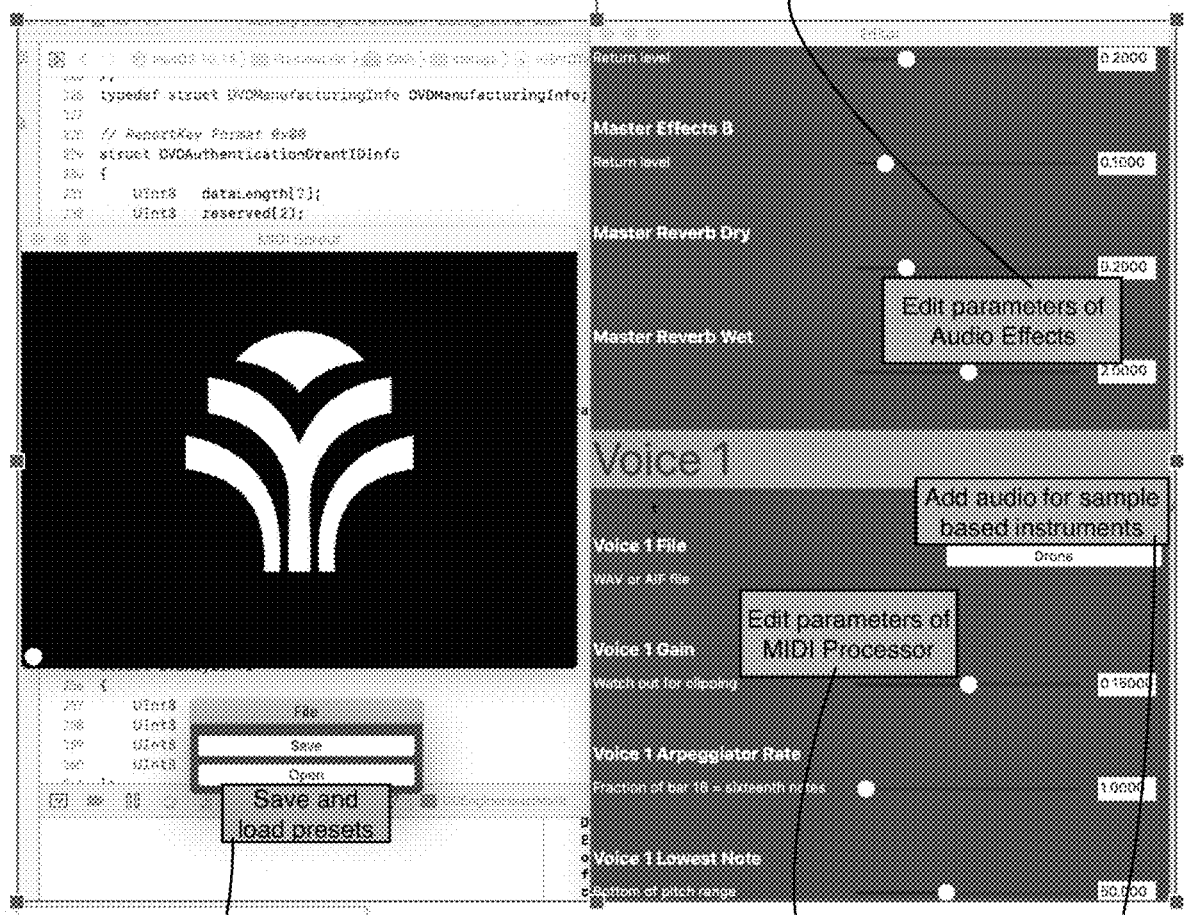
FIG. 5 represents an example of a graphical user interface of an example embodiment.

FIG. 5 shows an example graphical user interface (GUI) of the embodiment. The GUI provides buttons for saving and loading preset audio configurations 570 and allows the user to edit parameters of audio effects 576; edit parameters of MIDI processor 572; or add audio for sample-based instruments 574.

The invention claimed is:

1. A method for generating music from biofeedback comprising:
   receiving physiological signals from a biofeedback device worn by a person; and
   transforming said analyzed signals into MIDI note values by applying an algorithm comprising:
      measuring a first interbeat interval; and
      measuring a second interbeat interval; and
      determining the difference between said first and second interbeat interval; and
      applying a MOD function to the said difference; and
      assigning the result of said MOD function to MIDI a note value; and
   translating said analyzed signals into MIDI continuous control values by applying an algorithm comprising:
      calculating a point value by dividing 128 by a target number; and
      measuring a current value from said received signals from a biofeedback device; and
      multiplying said point value by said current value to obtain a MIDI continuous-control value; and
   determining tempo in beats per minute by a master clock; and
   sending at least one MIDI note value through a first MIDI channel; and
   sending at least one MIDI continuous-control value through a second MIDI channel; and
   applying MIDI effects to each of said first and second MIDI channels; and
   applying MIDI instruments to said applied MIDI effects of said first and second MIDI channels; and
   outputting said mixed audio through a speaker.

2. The method of claim 1 further comprising:
   sending MIDI note values and MIDI continuous-control values to a MIDI processor; and
   controlling pitch, timing and timbre qualities of digital instruments assigned to said MIDI note values and MIDI continuous-control values.

3. The method of claim 1 further comprising:
   applying a MOD-12 function to the said difference between said first and second interbeat interval; and
   assigning a MIDI note value from a 12-note scale to the result of said MOD-12 function; wherein
   notes selected from a 12-note scale are sent through said first MIDI channel.

4. The method of claim 1 further comprising:
   applying a MOD-36 function to the said difference between said first and second interbeat interval; and
   assigning at least one MIDI note value from a 36-note scale to the result of said MOD-36 function; wherein
   notes selected from a 36-note scale are sent through said first MIDI channel.

5. The method of claim 1 further comprising:
   applying a MOD-8 function to the said difference between said first and second interbeat interval; and
   assigning at least one MIDI note value from an 8 note scale to the result of said MOD-8 function; wherein
   notes selected from an 8-note scale is sent through said first MIDI channel.

6. The method of claim 1 further comprising:
   creating an audio master from said MIDI instruments applied to said MIDI effects; and
   mixing said audio master; wherein
   the mixed audio master is output through a speaker.

7. The method of claim 1 further comprising:
   Depicting parameters of audio effects and MIDI processor settings and sample-based instruments in a graphical user interface; and
   allowing a user to adjust audio effects and MIDI processor settings and to choose sample-based instruments, and to mix the sound that is output to a speaker.

8. The method of claim 1 further comprising:
   applying said MIDI effects to each of said first and second MIDI channels by scaling MIDI note values; and
   transposing MIDI note values; and
   arpeggiating MIDI note values.

* * * * *